US012714727B2

(12) United States Patent
Honmou et al.

(10) Patent No.: US 12,714,727 B2
(45) Date of Patent: Aug. 25, 2026

(54) PHARMACEUTICAL COMPOSITION FOR TREATING AMYOTROPHIC LATERAL SCLEROSIS

(71) Applicants: Sapporo Medical University, Sapporo (JP); Nipro Corporation, Osaka (JP)

(72) Inventors: Osamu Honmou, Hokkaido (JP); Masanori Sasaki, Hokkaido (JP); Yuko Sasaki, Hokkaido (JP); Shinichi Oka, Hokkaido (JP); Masahito Nakazaki, Hokkaido (JP); Rie Maezawa, Hokkaido (JP)

(73) Assignees: Sapporo Medical University, Hokkaido (JP); Nipro Corporation, Osaka (JP)

( * ) Notice: Subject to any disclaimer, the term of this patent is extended or adjusted under 35 U.S.C. 154(b) by 918 days.

(21) Appl. No.: 17/438,833

(22) PCT Filed: Mar. 13, 2020

(86) PCT No.: PCT/JP2020/012566
§ 371 (c)(1),
(2) Date: Sep. 13, 2021

(87) PCT Pub. No.: WO2020/184729
PCT Pub. Date: Sep. 17, 2020

(65) Prior Publication Data

US 2022/0133805 A1 May 5, 2022

(30) Foreign Application Priority Data

Mar. 14, 2019 (JP) ................................. 2019-046572

(51) Int. Cl.
*A61K 35/28* (2015.01)
*A61K 35/15* (2015.01)
*A61P 21/02* (2006.01)
*A61P 25/28* (2006.01)

(52) U.S. Cl.
CPC .............. *A61K 35/28* (2013.01); *A61K 35/15* (2013.01); *A61P 21/02* (2018.01); *A61P 25/28* (2018.01)

(58) Field of Classification Search
CPC ......... A61K 35/28; A61K 35/15; A61P 25/28; A61P 21/02
See application file for complete search history.

(56) References Cited

U.S. PATENT DOCUMENTS

2010/0254953 A1 10/2010 Honmou et al.
2011/0223205 A1* 9/2011 Gosiewska ............. A61P 25/02 424/93.21
2015/0209389 A1 7/2015 Gothelf et al.
2018/0296607 A1 10/2018 Gothelf et al.
2019/0117700 A1* 4/2019 Sapporo ............... A61K 9/0019
2019/0183937 A1 6/2019 Honmou et al.

FOREIGN PATENT DOCUMENTS

JP 2015-531594 A 11/2015
WO WO-2009/034708 A1 3/2009
WO WO-2013/082543 A1 6/2013
WO WO-2014/024183 A1 2/2014
WO WO-2017/188457 A1 11/2017
WO WO-2018/015945 A2 1/2018
WO WO-2018/034023 A1 2/2018
WO WO-2018/083700 A1 5/2018

OTHER PUBLICATIONS

Roche, et al., Brain (2012) 135(3): 847-852 (Year: 2012).*
Wexler, M., ALS News Today (2024) p. 1-11 (Year: 2024).*
Thomsen et al., eNeuro (2015) 2(3): 1-8 (Year: 2015).*
Bursch et al., "Analysis of the therapeutic potential of different administration routes and frequencies of human mesenchymal stromal cells in the SOD1G93A mouse model of amyotrophic lateral sclerosis," J. Tissue Eng. Regen. Med., Feb. 27, 2019, 13(4):649-663.
Ciervo et al., "Advances, challenges and future directions for stem cell therapy in amyotrophic lateral sclerosis," Molecular Neurodegeneration, Nov. 13, 2017, 12(1):1-22.
Gugliandolo et al., "Mesenchymal Stem Cells: A Potential Therapeutic Approach for Amyotrophic Lateral Sclerosis?", Stem Cells International, Mar. 10, 2019, 2019:3675627, 1-16.
Horita et al., "Intravenous Administration of Glial Cell Line-Derived Neurotrophic Factor Gene-Modified Human Mesenchymal Stem Cells Protects Against Injury in a Cerebral Ischemia Model in the Adult Rat," J. Neurosci. Res., Nov. 15, 2006, 84(7):1495-1504.
International Search Report dated Jun. 2, 2020, in PCT/JP2020/012566.
Kosuge et al., "Characterization of chronic glutamate-mediated motor neuron toxicity in organotypic spinal cord culture prepared from ALS model mice," Neuroscience Letters, Apr. 24, 2009, 454(2):165-169.
Nicaise et al., "Impaired blood-brain and blood-spinal cord barriers in mutant SOD1-linked ALS rat," Brain Research, Sep. 11, 2009, 1301:152-162.
Sasaki, Shoichi, "Alterations of the blood-spinal cord barrier in sporadic amyotrophic lateral sclerosis," Neuropathology, Aug. 4, 2015, 35(6):518-528.
Sun et al., "Multiple systemic transplantations of human amniotic mesenchymal stem cells exert therapeutic effects in an ALS mouse model," Cell and Tissue Research, Jun. 8, 2014, 357(3):571-582.
Uccelli et al.,. "Intravenous Mesenchymal Stem Cells Improve Survival and Motor Function in Experimental Amyotrophic Lateral Sclerosis," Molecular Medicine, Jul. 18, 2012, 18(1):794-804.
Winkler et al., "Blood-spinal cord barrier breakdown and pericyte reductions in amyotrophic lateral sclerosis," Acta Neuropathol., 2013 (Sep. 1, 2012), 125(1):111-120.

(Continued)

*Primary Examiner* — Evelyn Y Pyla
*Assistant Examiner* — Katherine R Small
(74) *Attorney, Agent, or Firm* — Foley & Lardner LLP

(57) ABSTRACT

The present invention relates to a pharmaceutical composition for treating amyotrophic lateral sclerosis. More specifically, the present invention relates to a pharmaceutical composition for treating amyotrophic lateral sclerosis, wherein the pharmaceutical composition comprises mesenchymal stem cells and is intravenously administered.

9 Claims, 14 Drawing Sheets

(56) References Cited

OTHER PUBLICATIONS

Winkler et al., "Blood-spinal cord barrier disruption contributes to early motor-neuron degeneration in ALS-model mice," PNAS, Mar. 3, 2014, 111(11):E1035-E1042.
Supplementary European Search Report dated Nov. 29, 2022 in EP 20771155.7.
Nabavi et al., "Safety, Feasibility of Intravenous and Intrathecal Injection of Autologous Bone Marrow Derived Mesenchymal Stromal Cells in Patients with Amyotrophic Lateral Sclerosis: An Open Label Phase I Clinical Trial," Cell J, Jan.-Mar. (Winter) 2019, 20(4):592-598.
Office Action dated Sep. 8, 2023 in SG 11202110033U.
Del Aguila et al., "Prognosis in amyotrophic lateral sclerosis, A population-based study," Neurology, 2003, 60:819-825.
Kim et al., "Dose-dependent efficacy of ALS-human mesenchymal stem cells transplantation into cisterna magna in SOD1-G93A Als mice," Neuroscience Letters, Jan. 14, 2010, 468(3):190-194.
Office Action dated Apr. 9, 2025 in EP 20771155.7.
Del Aguila et al., "Prognosis in amyotrophic lateral sclerosis, A population-based study," Neurology, 2003, 60:813-819.

* cited by examiner

Ventral horn in spinal cord
Normal
BBB score 21
Moderate
BBB score 11
End-stage
BBB score 0
Spinal cord
C1
T6
L4

(A)

(B)

PHARMACEUTICAL COMPOSITION FOR TREATING AMYOTROPHIC LATERAL SCLEROSIS

CROSS-REFERENCE TO RELATED APPLICATIONS

This application is the U.S. National Stage of PCT/JP2020/012566, filed Mar. 13, 2020, which claims priority to JP 2019-046572, filed Mar. 14, 2019.

TECHNICAL FIELD

The present specification includes the contents described in the specification of Japanese Patent Application No. 2019-046572 (filed on Mar. 14, 2019), based on which the priority of the present application is claimed.

RELATED APPLICATION

Technical Field

The present invention relates to a pharmaceutical composition for treating amyotrophic lateral sclerosis. More specifically, the present invention relates to a pharmaceutical composition for treating amyotrophic lateral sclerosis (ALS), wherein the pharmaceutical composition comprises mesenchymal stem cells and is intravenously administered.

Background Art

Amyotrophic lateral sclerosis (ALS) is a progressive neurodegenerative disease selectively damaging motor neurons and a serious disease of unknown cause for which no fundamental treatment has been found. ALS can be broadly divided into familial ALS and sporadic ALS. About 22% of familial ALS patients, who occupy about 5% of all patients, have been reported to have mutations in the superoxide dismutase (SOD1) gene. Other than SOD1, e.g., TDP43, FUS/TLS, and C9orf72 have been reported as causative genes for ALS.

Impairment of the blood-brain barrier (BBB) and blood-spinal cord barrier (BSCB) is known as one of the mechanisms common to ALS patients and ALS animal models. Since BBB/BSCB impairment observed from the early stages of ALS causes various neurological disorders, it is attracting attention as a cause of ALS (Non Patent Literatures 1 to 4). Since ALS is a complication having various symptoms such as neuroinflammation and motor neuron deficiency, effective treatment for these various symptoms is desired.

Mesenchymal stem cells (MSCs) are known to have neuroprotective and BBB repair effects. The inventors have reported that intravenous administration of MSCs to patients with cerebral infarction improves motor function and repairs lesion sites (Patent Literatures 1 to 3). They have also reported that intravenous administration of MSCs to patients with spinal cord injury results in functional recovery, accelerated axonal regeneration, and reduction of lesion sites (Patent Literatures 2 and 3).

MSCs are known to secrete a variety of neurotrophic factors. Among the neurotrophic factors, glial cell line-derived neurotrophic factor (GDNF) has been confirmed to have the effect of protecting motor neurons (Non Patent Literature 5). The inventors measured the amount of GDNF contained in the brain tissue (infarct region) of cerebral infarction model rats by ELISA and confirmed that the amount of GDNF is significantly higher in the MSC administration group than in the control group (Non Patent Literature 6). Gothelf et al. disclose a method for treating ALS by culturing MSCs in a differentiation medium containing bFGF and PDGF to induction-differentiate MSCs into cells that secrete neurotrophic factors and subarachnoidally or intramuscularly injecting the cells to ALS patient (Patent Literature 4). Lanza et al., disclose a pharmaceutical composition containing mesenchymal stromal cells obtained by differentiation induction from angioblastic cells, for treating unwanted immune response. ALS is also included in the list of target diseases, but no specific pharmacological effect is shown (Patent Literature 5).

CITATION LIST

Patent Literature

[Patent Literature 1] WO2009/034708

[Patent Literature 2] WO2017/188457

[Patent Literature 3] WO2018/034023

[Patent Literature 4] WO2014/024183 (Japanese Translation of PCT International Application Publication No. 2018-138044)

[Patent Literature 5] WO2013/082543 (Japanese Patent Laid-Open No. 2018-27954)

Non Patent Literature

[Non Patent Literature 1] Winkler et al., 2014, Proc. Natl. Acad. Sci., Vol. 111 (11): ppE1035-E1042

[Non Patent Literature 2] Winkler et al., 2013, Acta Neuropathologica, Vol. 125 (1): pp 111-120

[Non Patent Literature 3] Nicaise et al., 2009, Brain Res., Vol. 1301: pp 152-162

[Non Patent Literature 4] Sasaki et al., 2015, Neuropathology, Vol. 35 (6): pp 518-528

[Non Patent Literature 5] Kosuge et al., 2009, Neurosci. Letters, Vol. 454 (2): pp 165-169

[Non Patent Literature 6] Horita et al., 2006, J. Neurosci, Res. Vol. 84 (7): pp 1495-1504

SUMMARY OF INVENTION

Technical Problem

An object of the present invention is to provide a new means for treating various symptoms of amyotrophic lateral sclerosis (ALS).

Solution to Problem

Using ALS model rats, the inventors evaluated the natural course of symptoms widely in view of motor function and histology, and found that intravenous administration of MSCs allows suppression of progression and alleviation of symptoms in both moderate and severe stages. They further studied more effective administration methods and achieved the present invention.

More specifically, the present invention relates to the following (1) to (6).

(1) A pharmaceutical composition for treating amyotrophic lateral sclerosis (ALS), wherein the pharmaceutical composition comprises mesenchymal stem cells and is intravenously administered.

(2) The pharmaceutical composition according to (1), which is administered twice or more.

(3) The pharmaceutical composition according to (1) or (2), wherein $10^6$ or more mesenchymal stem cells are administered per dose.

(4) The pharmaceutical composition according to any one of (1) to (3), wherein the mesenchymal stem cells are mesenchymal stem cells derived from bone marrow or blood.

(5) The pharmaceutical composition according to any one of (1) to (4), wherein the mesenchymal stem cells are mesenchymal stem cells derived from the bone marrow or blood of a patient.

(6) The pharmaceutical composition according to any one of (1) to (5), wherein the mesenchymal stem cells are CD24-negative.

Advantageous Effects of Invention

The pharmaceutical composition of the present invention can be expected to prevent neurological disorders by suppressing impairment of BBB/BSCB and enhancing the expression of neurotrophic factors. The pharmaceutical composition of the present invention can suppress motor deterioration and extend the survival period regardless of a degree of symptom progression, so that the composition can be an effective method for treating ALS.

DESCRIPTION OF EMBODIMENTS

1. Amyotrophic Lateral Ssclerosis

Figure 1:
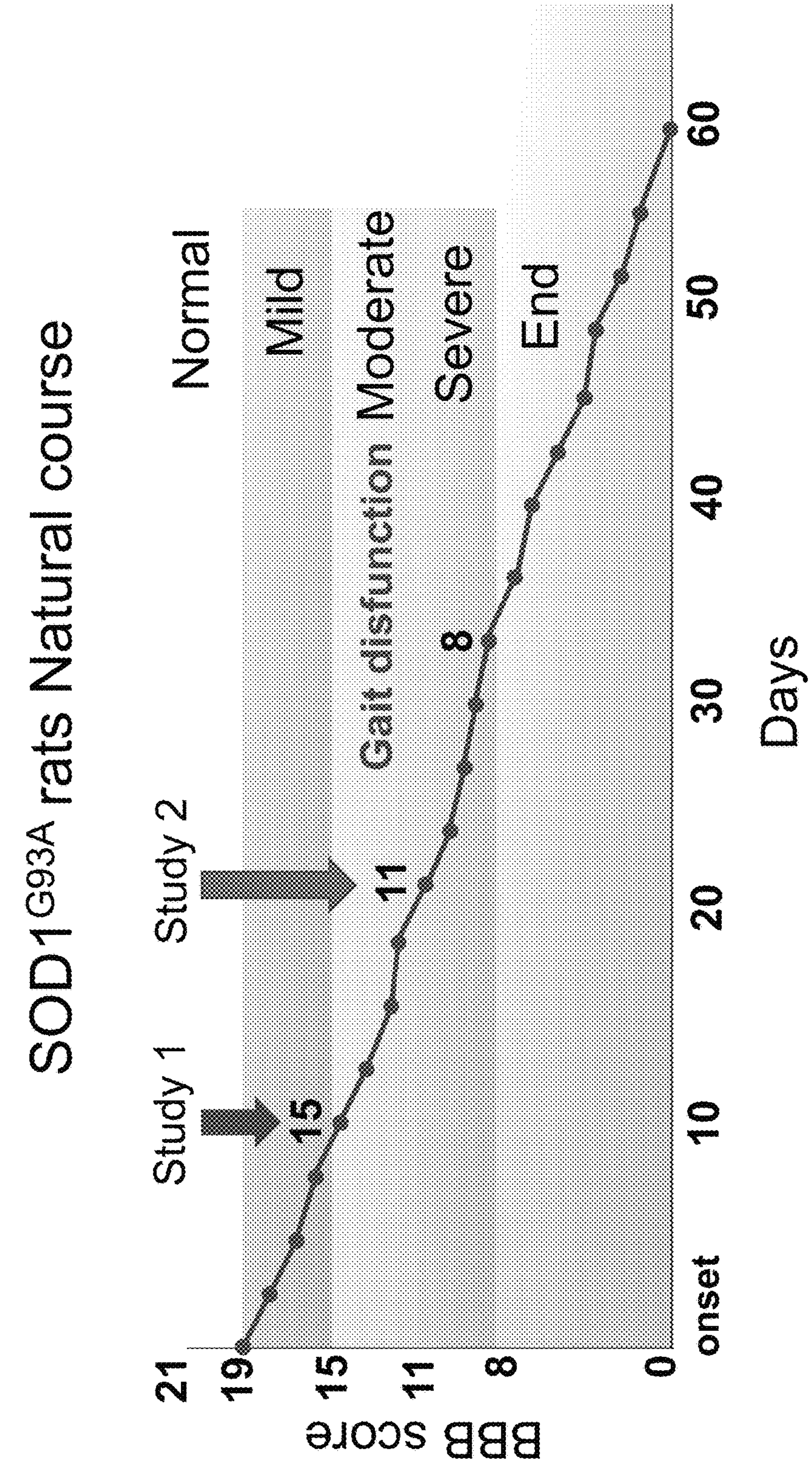
FIG. 1 shows natural course of ALS model rats ($SOD1^{G93A}$ mutant transgenic rats) based on behavioral evaluation. The vertical axis represents the BBB score and the horizontal axis represents the number of days.

Amyotrophic lateral sclerosis (ALS) is a progressive neurodegenerative disease selectively damaging motor neurons. ALS can be broadly divided into familial ALS and sporadic ALS and most cases of ALS are sporadic (95%). ALS is progressive. When affected with ALS, symptoms are not ameliorated and muscles throughout the body gradually become immobile; finally leading to death due to respiratory failure. At present, ALS is a disease of unknown cause and a fundamental treatment thereof has not yet been found.

Recently, neuropathy caused by impairment of the blood-brain barrier (BBB) and the blood-spinal cord barrier (BSCB) have attracted attention as one of the causes of ALS. MSCs are known to secrete a wide variety of neurotrophic factors, and the inventors have found that intravenous administration of MSCs increases the level of GDNF expression at affected sites. They further have confirmed that intravenous administration of MSCs increases the expression level of a member of the GDNF family, Neurturin (Nrtn), at affected sites (see, Examples described later).

2. Mesenchymal Stem Cells

The "mesenchymal stem cells" used in the pharmaceutical composition of the present invention refer to stem cells having pluripotent and self-renewal ability and present in an extremely small amount in stromal cells of the mesenchymal tissue. It is known that mesenchymal stem cells not only differentiate into connective tissue cells such as osteocytes, chondrocytes, and adipocytes, but also have the ability to differentiate into nerve cells and myocardial cells.

As a source for mesenchymal stem cells, cells obtained by differentiation induction from ES cells or induced pluripotent stem cells (iPS cells), established cells and cells isolated and proliferated from a living organism, can be used. In the case of the living organism, bone marrow, peripheral blood, umbilical blood, fetal embryo and brain may be mentioned. Mesenchymal stem cells derived from bone marrow or blood, particularly mesenchymal stem cells of bone marrow, and more particularly, mesenchymal stem cells of human bone marrow are preferred. The mesenchymal stem cells derived from bone marrow have the following advantages: 1) remarkable effect can be expected, 2) risk of side effects is low, 3) sufficient supply of donor cells is expected, 4) non-invasively treated and autologous transplantation can be made, 5) risk of infection is low, 6) less possibility of immune rejection, 7) no ethical issues, 8) socially acceptable, 9) widely and easily accepted as a general medical treatment. Furthermore, bone marrow transplantation is a therapy already and actually employed in clinical sites and its safety has been also confirmed. Moreover, bone marrow-derived stem cells are highly migratory and reach a target damage tissue not only by local transplantation but also intravenous administration, and thus, a therapeutic effect can be expected.

Cells may be derived from allogeneic or autologous cells; however, mesenchymal stem cells derived from autologous cells (derived from cells of a patient oneself) are preferred.

The mesenchymal stem cells used in the present invention are preferably undifferentiated. This is because undifferentiated cells have a high proliferation rate and a survival rate after introduced into a living body. The undifferentiation state of cells can be checked by being negative to a differentiation marker, CD24. The inventors have developed a method for obtaining such cells and the details thereof are described in WO2009/002503.

In the method developed by the inventors, cells are separated from, e.g., bone marrow fluid in such a condition that they are not substantially in contact with an anticoagulant (e.g., heparin), proliferated in a medium containing allogeneic serum (preferably, autologous serum; human serum in the case of a human pharmaceutical composition) in the absence of an anticoagulant (e.g., heparin) or in the presence of an extremely low concentration of the anticoagulant. The phrase "in the absence of an anticoagulant or in the presence of an extremely low concentration of the anticoagulant" means that the anticoagulant is not contained in such an amount that produces an effect as an anticoagulant. More specifically, for example, heparin or a derivative thereof, which is usually effective in an amount of about 20 to 40 μ/mL. In the method developed by the inventors, the mount thereof previously added to a blood collection tube for collecting a sample is minimized. Owing to this, the amount thereof in the sample taken from a living body becomes less than 5 U/mL, preferably less than 2 U/mL, and further preferably less than 0.2 U/mL. As a result, the amount thereof present in a medium for culturing cells becomes less than 0.5 U/mL, preferably less than 0.2 U/mL, and further preferably less than 0.02 U/mL relative to the volume of the medium (see, WO2009/034708).

The density of cells in a medium has an effect on the property of cells and differentiation direction. In the case of mesenchymal stem cells, if the density of the cells in the medium exceeds 8,500 cells/cm$^2$, the property of mesenchymal stem cells will change. For the reason, the density of the cells to be subcultured is preferably at most 8,500 cells/cm$^2$ or less; and more preferably, at the time point when the density of the cells reaches 5,500 cells/cm$^2$ or more, the cells are subjected to subculture.

In the method developed by the inventors, a human serum-containing medium is used, so that a medium is desirably exchanged as few times as possible in consideration of burden on a serum donor. A medium is exchanged at a frequency of, for example, at least once a week, more preferably once or twice a week.

In culture, cells are repeatedly subcultured until the total number of cells reaches $10^8$ or more. The requisite number of cells may vary depending on the intended use. The number of mesenchymal stem cells required in transplantation for treating an ischemic brain disease such as cerebral infarction, is $10^7$ or more, and conceivably $10^6$ or more in the present invention. According to the method developed by the inventors, $10^7$ mesenchymal stem cells can be obtained for about 12 days.

The mesenchymal stem cells proliferated, if necessary, may be stored by a procedure such as cryopreservation (for example, in a deep freezer of −152° C.) until use. For cryopreservation, a medium (medium for mammalian cells, such as RPMI) containing serum (preferably human serum, more preferably autologous serum), dextran and DMSO, is used as a cryopreservation solution. For example, cells are suspended in a cryopreservation solution containing ordinary filter-sterilized RPMI (20.5 mL), autologous serum (20.5 mL) taken from a patient, dextran (5 mL) and DMSO (5 mL), and cryopreserved at −150° C. Examples of DMSO that can be used include, but are not limited to, Cryoserve® manufactured by NIPRO CORPORATION and low-molecular Dextran L injection manufactured by Otsuka Pharmaceutical Co., Ltd.

The mesenchymal stem cells prepared as mentioned above may be checked for quality and function by confirming a) that mesenchymal stem cells express CX3CL1 after adding cytokines to a culture containing mesenchymal stem cells; or b) that mesenchymal stem cells express EGFR and/or ITGA4.

Examples of "inflammatory cytokines" that are used include TNF-α, INFγ, IL-1, IL-6, IL-8, IL-12 and IL-18. Of them, preferably TNF-α, INFγ, and IL-6 are included; and more preferably a mixture of TNF-α, INFγ, and IL-6 is used.

The aforementioned method may further include a step of confirming the presence of at least one selected from BDNF, VEGF, and HGF in a culture (in the absence of cytokines). In particular, it is important to confirm the presence of BDNF and/or VEGF, and the most important to confirm the presence of BDNF.

If mesenchymal stem cells express CX3CL1 by the addition of inflammatory cytokines, it can be expected that the mesenchymal stem cells will have an excellent inflammation regulatory effect (immunoregulatory function). If 90% or more of mesenchymal stem cells express EGFR and/or ITGA4, the mesenchymal stem cells are expected to have excellent accumulation ability at lesion sites. In addition, if any of the neurotrophic factors such as BDNF, VEGF, and HGF, exists in the medium, it can be expected that mesenchymal stem cells having a high neuroprotective effect are contained. Of them, the presence of BDNF and/or VEGF, especially BDNF, can serve an important index for the presence of MSCs having a high neuroprotective effect. Mesenchymal stem cells secrete BDNF, VEGF and/or HGF even if they are not stimulated. Thus, the secretory ability may be evaluated based on secretion from unstimulated cells or from stimulated cells with inflammatory cytokines.

The expression of CX3CL1, EGFR, ITGA4, BDNF, VEGF or HGF is preferably confirmed at the protein level rather than the gene level. In the case of a cell surface protein such as EGFR or ITGA4, flow cytometry (FCM) is preferably used for measurement in consideration of simplicity and sensitivity; whereas, in the case of a secretory protein such as CX3CL1, BDNF, VEGF or HGF, bead assay is preferably employed in consideration of convenience and sensitivity.

3. Pharmaceutical Composition of the Present Invention

The pharmaceutical composition of the present invention containing mesenchymal stem cells and to be intravenously administered for treating ALS.

The larger the number of mesenchymal stem cells contained in the pharmaceutical composition of the present invention, the more preferable; however, it is practical that the cells are contained in the minimum amount enough to exert an effect in consideration of the timing of administration to a patient and the time required for culturing. Accordingly, in a preferred embodiment of the pharmaceutical composition of the present invention, the number of mesenchymal stem cells contained per dose is $10^6$ or more, preferably $5\times10^6$ or more, more preferably $10^7$ or more, more preferably $5\times10^7$ or more, more preferably $10^8$ or more, and further preferably $5\times10^8$ or more.

The pharmaceutical composition of the present invention may be a formulation for intravenous administration. The formulation for intravenous administration is an aqueous or non-aqueous isotonic aseptic solution or suspension and used in combination appropriately with a pharmacologically acceptable carrier or medium, more specifically, sterilized water, saline, culture medium (particularly, a medium, e.g., RPMI for use in culture of mammalian cells), a physiological buffer such as PBS, a vegetable oil, an emulsifier, a suspension, a surfactant, a stabilizer, an excipient, a vehicle, a preservative and a binder to be formulated into an appropriate unit-dosage form.

As an aqueous solution for injection, a physiological buffer such as saline, a culture medium and PBS, and an isotonic solution containing glucose and other supplements such as D-sorbitol, D-mannose, D-mannitol and sodium chloride, are mentioned and these may be used in combination with an appropriate dissolution aid such as an alcohol, e.g., ethanol, polyalcohol, propylene glycol, polyethylene glycol and a nonionic surfactant such as polysorbate 80 and HCO-50.

It does not matter whether ALS to be treated by administration of the pharmaceutical composition of the present invention is familial ALS or sporadic ALS and mild or severe. In the case of mild ALS, improvement of symptoms and suppression of progression can be expected by administration of the pharmaceutical composition of the present invention. In the case of moderate to severe ALS, suppression of progression can be expected.

The pharmaceutical composition of the present invention is not particularly limited in dosing frequency and interval, and can be repeatedly administered a plurality of times, for example, two or more, 3 or more, 4 or more and 5 or more, as long as a therapeutic effect can be expected. After the initial administration, the composition may be administered every time the symptoms progress or at regular intervals. The administration interval may vary depending on the symptoms and fall in the range of 1 month to 10 years, for example, 1 month, 2 months, 3 months, 4 months, 6 months, 1 year, 2 years, 3 years to 10 years. The symptoms can be kept in a good condition and the survival period can be extended by repeatedly administering the composition.

The pharmaceutical composition of the present invention can be used also in combination with, e.g., known ALS therapeutic agents such as riluzole, edaravone, penicillin and a β-lactam antibiotic.

The pharmaceutical composition of the present invention can suppress impairment of BBB/BSCB, promote expression of neurotrophic factors, and suppress neurological disorders. The pharmaceutical composition of the present invention can suppress motor deterioration regardless of the degree of symptom progression and extend the survival period.

EXAMPLES

Now, the present invention will be more specifically described with reference to Examples, but the present invention is not limited to these Examples.

Reference Example 1

Preparation of Rat Bone Marrow-Derived Mesenchymal Stem Cells

The MSCs used in the following examples were prepared in the following manner in accordance with previous reports.

The experiment was carried out in accordance with the animal experiment manual of Sapporo Medical University. Bone marrow was obtained from the femur of a mature SD rat and diluted up to 25 ml with Dulbecco's Modified Eagle's Medium (DMEM) in accordance with previous reports. To the dilution solution, heat-inactivated 10% FBS, 2 mM L-glutamine, 100 U/ml penicillin, and 0.1 mg/ml streptomycin were added. The mixture was incubated at 37° C. for 3 days under a 5% $CO_2$ atmosphere (Kim S. et al., Brain Res. 2006; 1123: 27-33. Ukai R. et al., J. Neurotrauma. 2007; 24: 508-520). After the culture was continued until confluent, adherent cells were removed with trypsin-EDTA and subcultured 3 times at a density of $1\times10^4$ cells/ml to obtain mesenchymal stem cells (MSC).

Example 1: Natural Course of ALS Model Rrat

1. Behavioral Evaluation

Method

ALS model rats (SOD1 rat (SD Tg (SOD1G93A) L26H)) were purchased from Taconic Biosciences and subjected to behavioral evaluation. SOD1 rats are known to have the SOD1 gene mutation (SOD1G93A) and extremely satisfactorily reproduce the pathology of human ALS (https://www.taconic.com/rat-model/sodl-rat).

Results

Onset emerged as tail down or gait dysfunction of the hindlimbs, which rapidly progressed to hindlimb paralysis (about 10 days). At moderate stage (BBB score: 15 to 11), initial paralysis was typically observed in one of the legs of the rats. In severe stage (BBB score: 10 to 8), both legs were paralyzed, but the forelimbs could be used for walking. At the end-stage, loss of righting reflex was observed in the rats (FIG. 1).

2. Histological Evaluation

Method

To histologically evaluate the natural course of ALS model rats, spinal cord of rats having BBB scores (indicators of hindlimb motor function evaluation) of 21, 11, and 0, were subjected to Kluver-Barrera staining (hereinafter referred to as KB staining) to stain nerve cells and myelin sheath and observe changes in the number of motor neurons. BBB scoring is a method of evaluating the motor function of the hindlimbs by placing rats in an open field and allowing them to freely move for 5 minutes (score of normal function: 21; the score decreases with symptomatic worsening; score of difficulty in walking: 11; and the worst score was 0, indicating "unable to walk").

ALS model rats were deeply anesthetized with anesthetics (ketamine 100 mg/kg, xylazine 20 mg/kg) and fixed by perfusion with 0.1 M phosphate buffer containing PBS and 4% paraformaldehyde (4% PFA). The spinal cord was taken out, separately cut into C1, T6, and L4 regions and fixed overnight with 4% PFA. After fixing, the regions were embedded in paraffin and sectioned into cut pieces of 10 μm in thickness, which were attached to slide glasses. Thereafter, the cut pieces were stained with KB and photographed under a fluorescence microscope (KEYENCE BZ9000).

Results

Figure 2:
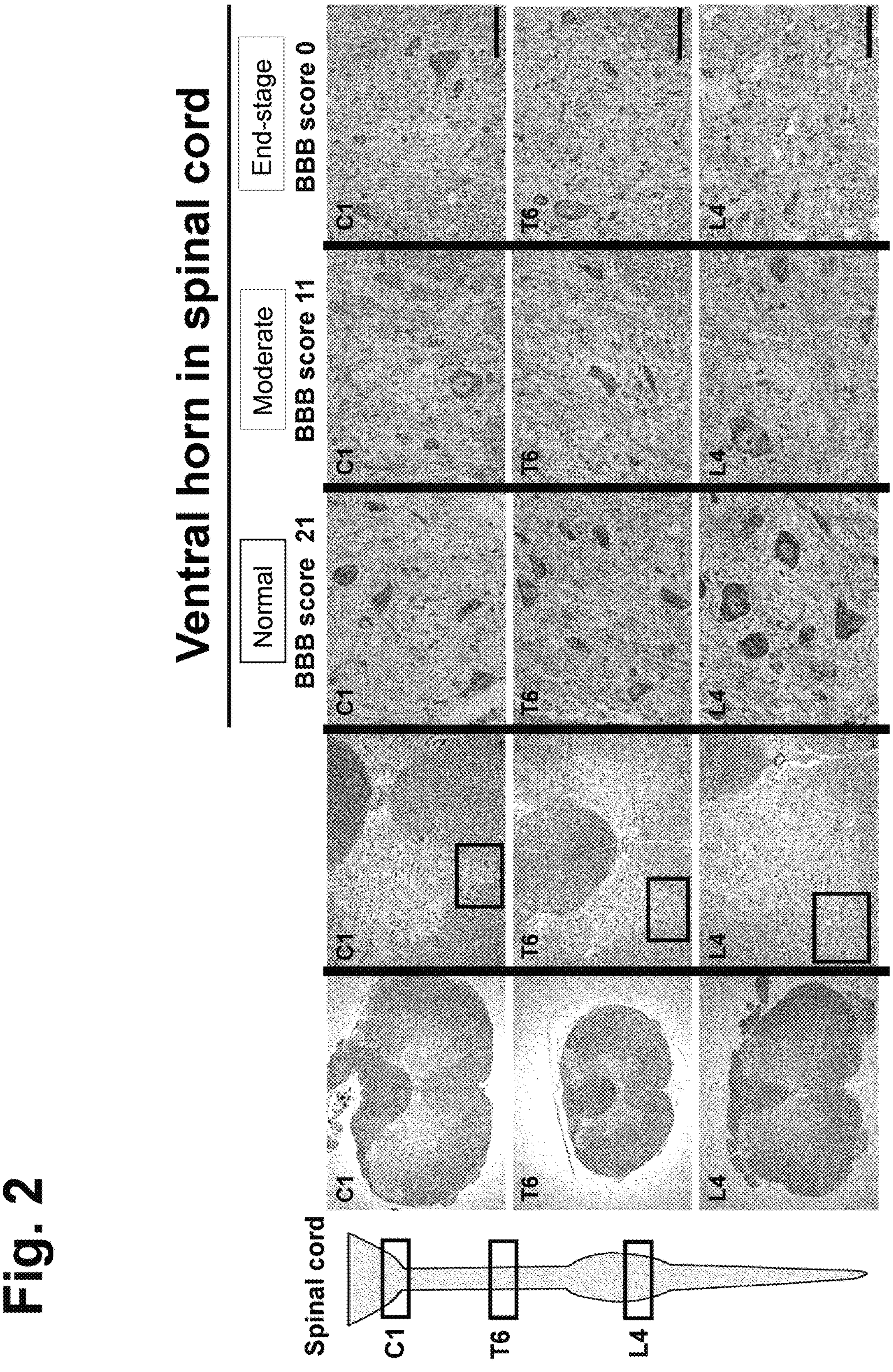
FIG. 2 shows tissue images of ALS model rats (stained with KB). Dark grey represents nerve cells and glial cells (small cells) and light grey represents myelin sheath.

Stained images are shown in FIG. 2. With progression of symptoms from Normal (BBB score 21) to Moderate (BBB score 11), the number of motor neurons (large cells of 700 $\mu m^2$ or more) decreased in all of the cervical spinal cord (C1), thoracic spinal cord (T6), and lumbar spinal cord (L4). Furthermore, residual nerve cells were confirmed in the rat's cervical spinal cord and thoracic spinal cord in the end-stage (BBB score 0); however, in the lumbar spinal cord, nerve cells almost completely disappeared.

Example 2: Effect of MSC Intravenous Administration in ALS Model rat (Study 1: Moderate Stage)

1. Behavioral Evaluation

Method

ALS model rats having a BBB score reduced to 15 were divided into two groups, an MSC-administration group (n=6) and a vehicle-administration group (n=13). To the MSC-administration group, a solution prepared by dissolving MSCs ($1.0\times10^6$) in 1 mL of a vehicle (fresh DMEM) was intravenously administered from the femoral vein. To the vehicle-administration group, 1 mL of DMEM was intravenously administered. The immunosuppressant cyclosporin A (10 mg/kg) was intraperitoneally administered to all rats every day from the day before MSC and vehicle administration until reaching the end-stage. Behavior was evaluated based on the BBB scores. The rats were placed in an open field at least twice a week and allowed to freely move around for 5 minutes, and then, the motor function of the hindlimbs was evaluated. The evaluator was not informed which treatment group the rat belonged to.

Results

Figure 3:
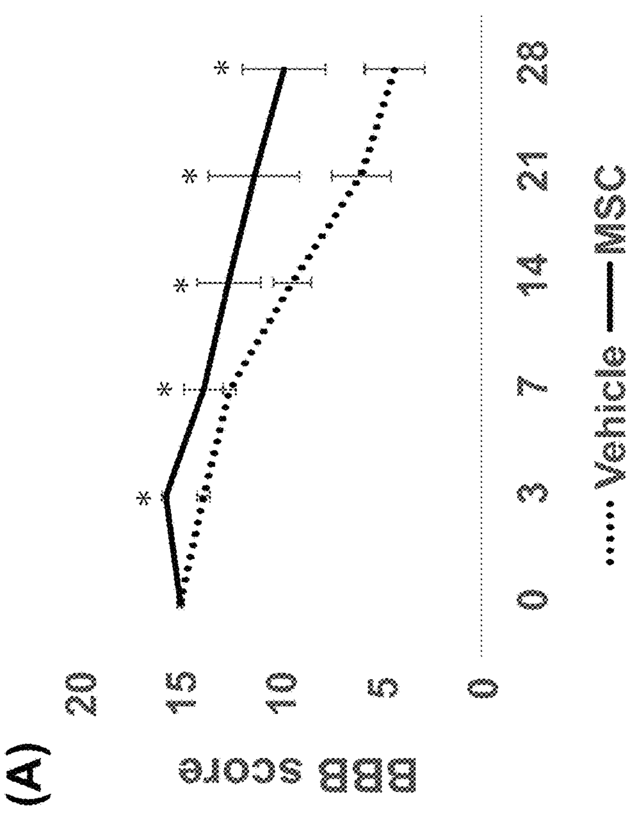
FIG. 3 shows behavioral evaluation of ALS model rats (moderate stage). (A) shows BBB score (solid line: MSC administration group; dashed line: vehicle administration group); and (B) shows BBB score alteration (solid bar: MSC administration group; open white bar: vehicle administration group).
Figure 3:
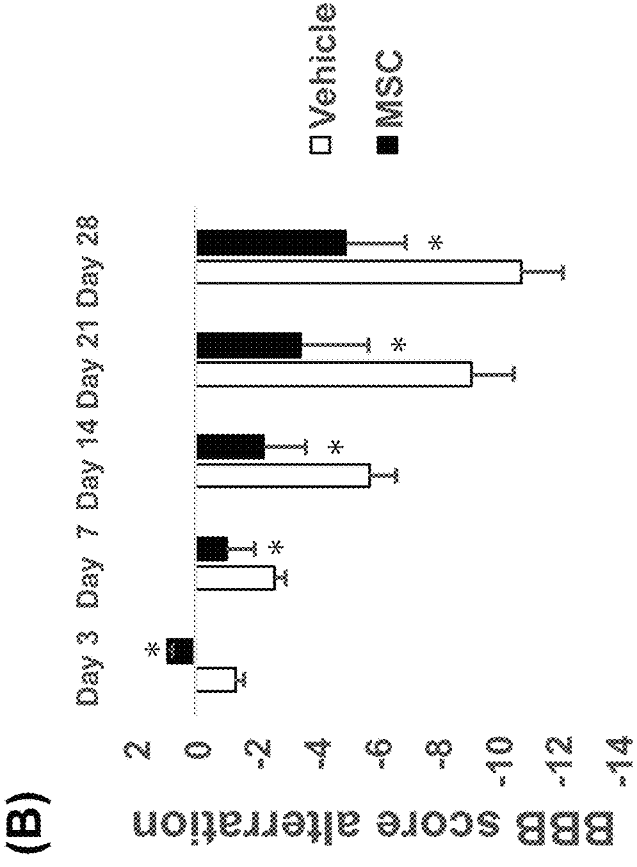

The decrease in BBB score was significantly suppressed in the MSC-administration group (FIG. 3 (A)). In particular, according to the evaluation on Day 3 of administration, improvement of symptoms was observed in the MSC-administration group. The BBB score alteration is shown therein. The BBB score alteration was smaller in the MSC-administration group than in the vehicle-administration group (FIG. 3 (B)).

2. Survival Period

Method

For rats subjected to behavioral evaluation, the survival rate in the period of 40 days after MSC or vehicle administration was evaluated by use of the Kaplan-Meier curve.

Results

Figure 4:
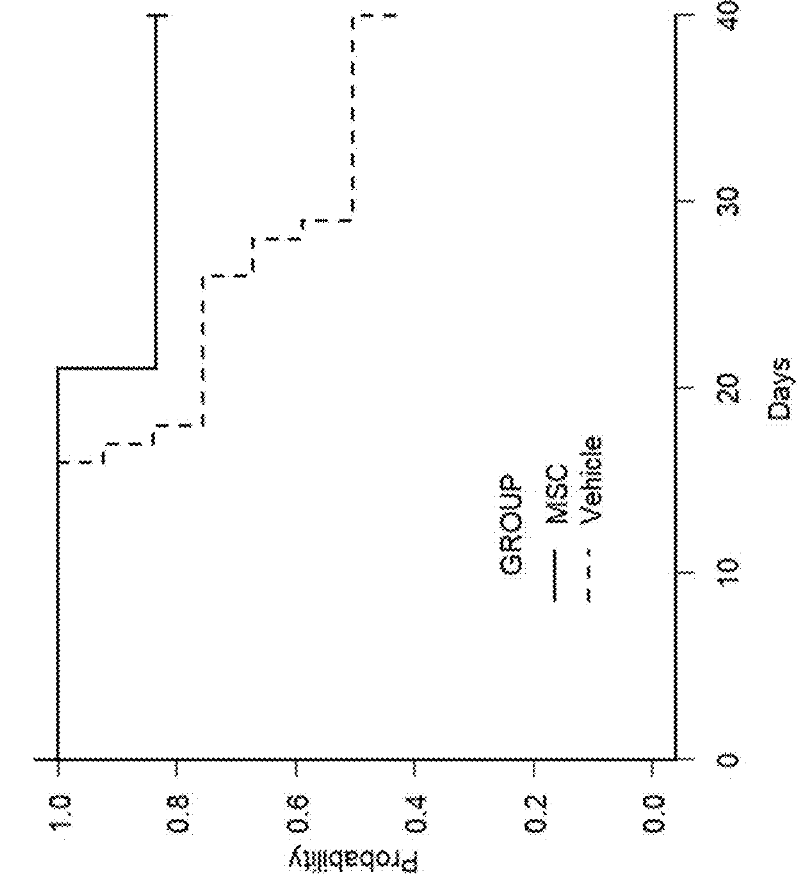
FIG. 4 shows evaluation of the survival period of ALS model rats (moderate stage). (A) shows the Kaplan-Meier curve (solid line: MSC administration group; dashed line: vehicle administration group); and (B) shows the survival rate after 40 days (solid bar: MSC administration group; open white bar: vehicle administration group).
Figure 4:
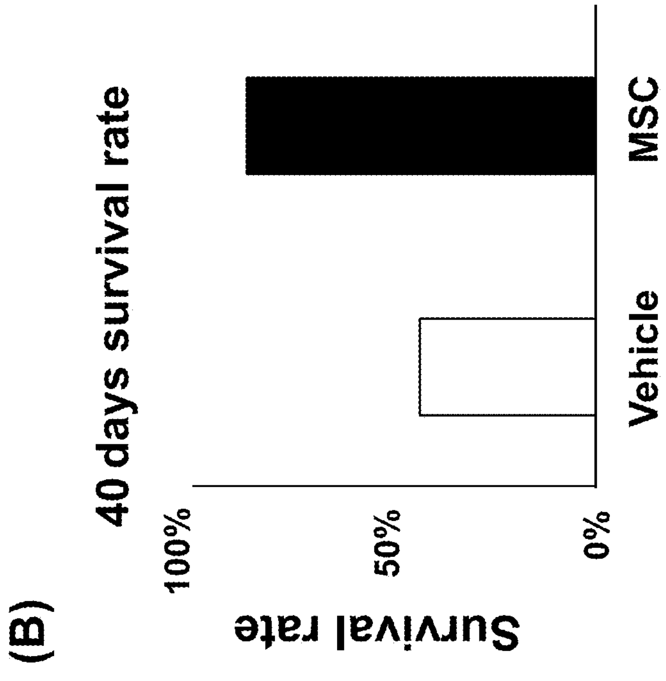

After 40 days, more than half of the rats died in the vehicle-administration group, but more than 80% of the rats survived in the MSC-administration group (FIG. 4).

3. Number of Spinal Motor Neurons

Method

ALS model rats having a BBB score reduced to 15 were divided into two groups, an MSC-administration group (n=3) and a vehicle-administration group (n=6). MSCs or a vehicle was administered in the same manner as above, and spinal cord (lumbar) ventral horn motor neurons were compared on Day 14 after administration. The immunosuppressant cyclosporin A (10 mg/kg) was intraperitoneally administered to all rats every day from the day before MSC and vehicle administration to the final evaluation day, i.e., Day 14 after administration. Motor neurons were defined as the cells having an area of 700 $\mu m^2$ or more.

Results

Figure 5:
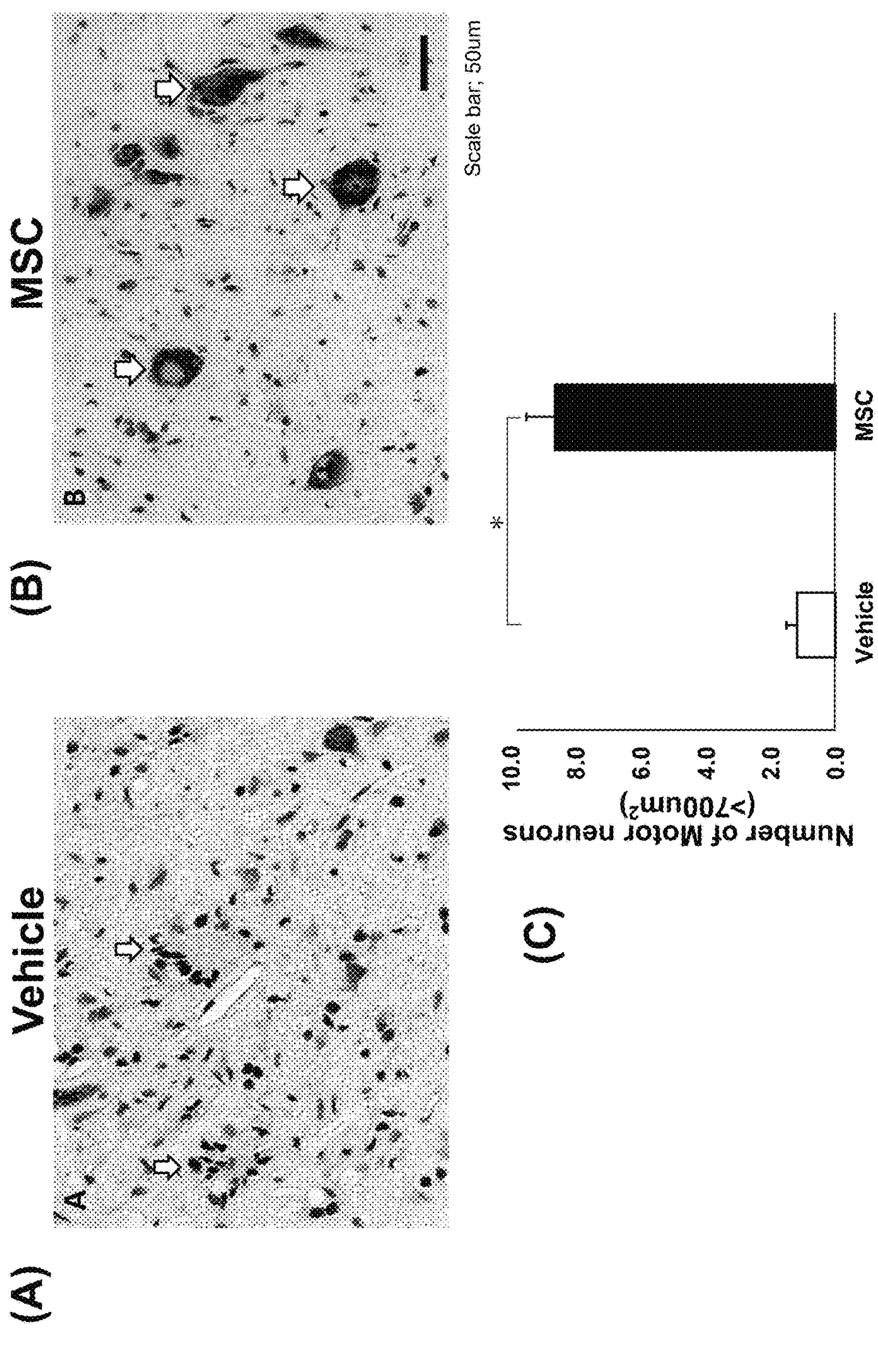
FIG. 5 shows evaluation of the number of motor neurons of the spinal cord in ALS model rats (moderate stage); more specifically, tissue images of the ventral horn of the spinal cord (lumbar spinal cord) on Day 14 after administration ((A) vehicle administration group, (B) MSC administration group (arrows point to motor neurons), and (C) a graph of the number of motor neurons (solid bar: MSC administration group; open white bar: vehicle administration group)).
Figure 6:
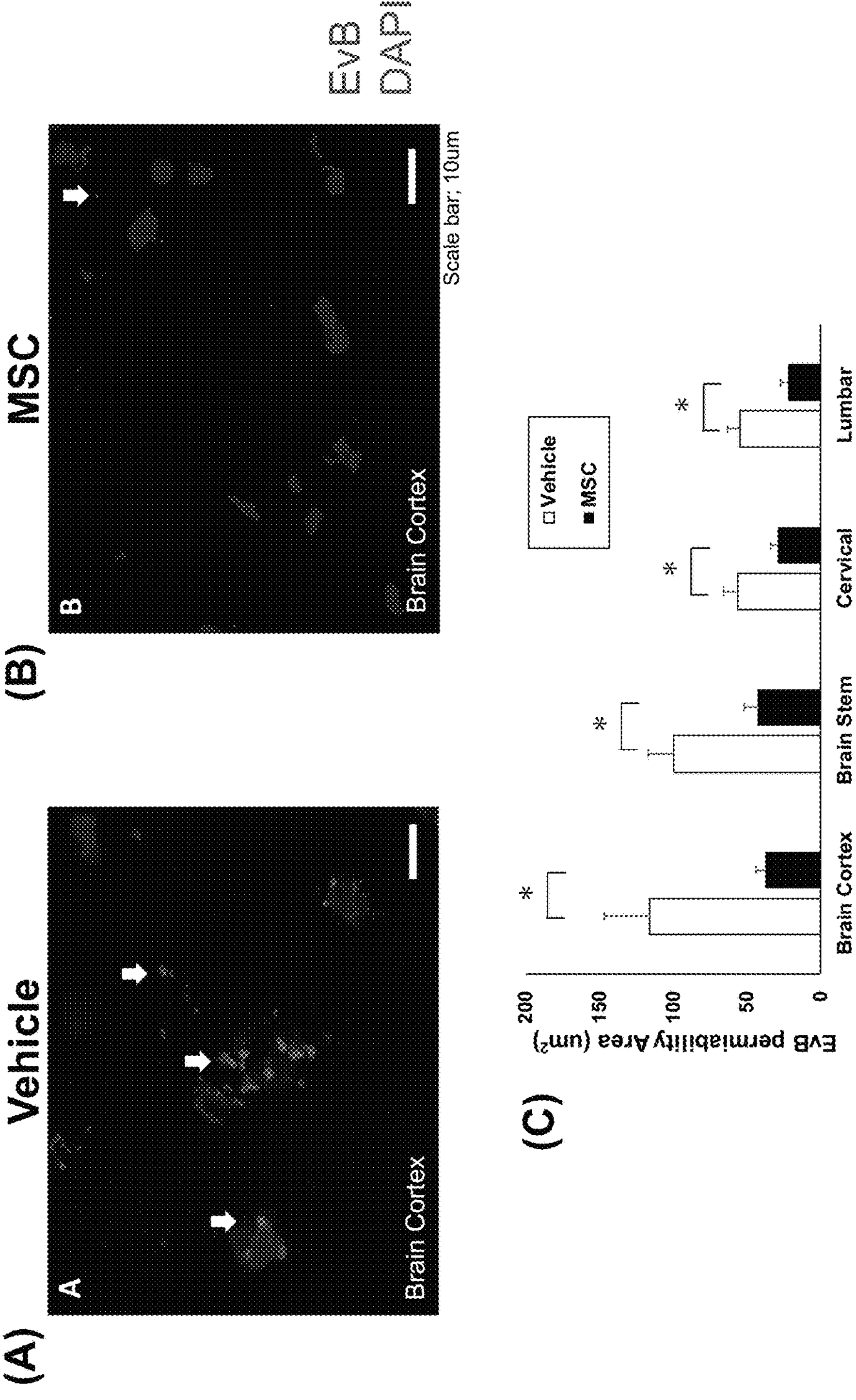
FIG. 6 shows evaluation of BBB/BSCB impairment of ALS model rats (moderate stage). Stained image of the brain cortex ((A) vehicle administration group, (B) MSC administration group, arrows point to motor neurons); (C) the area of the region where Evans blue leaked (solid bar: MSC administration group; open white bar: vehicle administration group; the regions of the sites of the brain cortex, brain stem (medulla oblongata), cervical spinal cord and lumbar spinal cord where Evans blue leaked, are shown sequentially from the left).

Significantly a large number of motor neurons were kept in the MSC-administration group compared to the vehicle-administration group (FIG. 5).

4. Impairment of Blood-Brain Barrier/Blood-Spinal Cord Barrier (BBB/BSCB)

Method

ALS model rats having a BBB score reduced to 15 were divided into two groups, an MSC-administration group (n=4) and a vehicle-administration group (n=4). MSCs or a vehicle was administered in the same manner as above. On Day 14 after administration, 4% Evans blue (EvB, Sigma, 4 ml/kg) was administered via the tail vein to individual rats in order to evaluate impairment of blood-brain barrier/blood-spinal cord barrier (BBB/BSCB). One hour later, ALS model rats were deeply anesthetized with anesthetics (ketamine 100 mg/kg, xylazine 20 mg/kg) and fixed by perfusion with PBS and 4% PFA. The brain and the spinal cord were taken out, separately cut into four sites: the brain, brain stem (medulla oblongata), cervical spinal cord and lumbar spinal cord, which were separately embedded in OCT compound and frozen in acetone cooled to −80° C. Nine sections of 20 μm in thickness were cut out at intervals of 100 μm by use of Cryostat, and attached to slide glasses. Counterstaining was carried out with DAPI and cover slides were applied by use of VECTASHIELD (Vector Laboratories). The sections were observed by a confocal microscope and the area of Evans blue leaked out of the blood vessel was measured using Image J software (NIH). Ex/Em (405 nm for DAPI, 488 nm for FITC-lectin, and 561 nm for EvB; LSM780 ELYRA S.1 system, Zeiss).

Results

Figure 7:
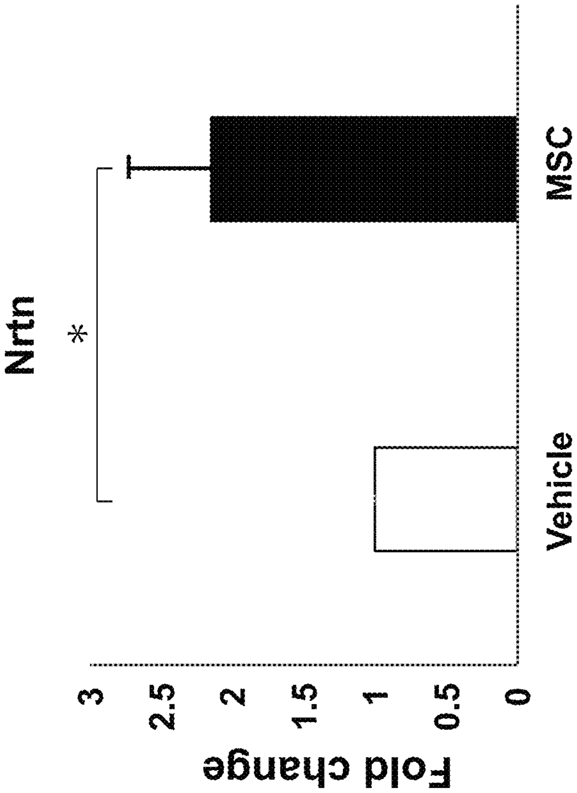
FIG. 7 shows the expression level (fold change) of Nrtn measured by quantitative RT-PCR (solid bar: MSC administration group; open white bar: vehicle administration group).

It was confirmed that there was significantly less leakage of Evans blue in the MSC-administration group in all of the cerebral cortex, brain stem (medulla oblongata), cervical spinal cord, and lumbar spinal cord. Thus, it was confirmed that the impairment of BBB/BSCB was suppressed or repaired (FIG. 7).

5. Nrtn Expression Analysis (Quantitative RT-PCR)

Method

ALS model rats having a BBB score reduced to 15 were divided into two groups, an MSC-administration group (n=4) and a vehicle-administration group (n=4), and MSCs or a vehicle was administered in the same manner as above. Twenty-four hours later, the rats were deeply anesthetized with anesthetics. The spinal cord (lumbar spinal cord) was taken out and RNA was extracted by use of RNeasy Plus mini kit (QIAGEN, Venlo, the Netherlands). RNA quality was checked based on the RIN number by use of Bioanalyzer RNA 6000 nano kit (Agilent Technologies, Santa Clara, CA, USA), and samples having a RIN number >8.0 were only used. Quantification was performed by the qRT-PCR method using TaqMan (registered trademark) Universal Master Mix II with Uracil-N glycosylase (UNG) and TaqMan (registered trademark) Gene Expression assays (Gapdh, Rn01775763_g1; Nrtn) and PRISM7500 with 7500 software v2.3 (Thermo Fisher Scientific Inc.). The gene expression ratio of the MSC-administration group was compared to that of the vehicle-administration group (n=4) in accordance with ΔΔCt method using Gapdh as an endogenous control. The thermal cycler protocol is as follows: a cycle consisting of a reaction at 50° C. for 2 minutes, a reaction at 95° C. for 10 minutes, a reaction at 95° C. for 15 seconds and a reaction at 60° C. for one minute, is repeated 40 times.

Results

The expression level of Nrtn was significantly high in the MSC-administration group (FIG. 7). Nrtn is a member of the GDNF family, and the mRNA expression of Nrtn was confirmed to significantly increase in the MSC-administration group. These results suggest that MSC transplantation exerts a neurotrophic effect on motor neurons in the ventral horn of the spinal cord, and, in a histological point of view, the number of residual neurons increases, which conceivably leads to a therapeutic effect on neurological symptoms.

Example 3: Effect of Intravenous MSC Administration to ALS Model Rat (Study 2: Severe Stage)

Method

ALS model rats with severe motor dysfunction with a low BBB score of 11 were divided into two groups. To the MSC-administration group (n=6), a solution prepared by dissolving MSCs ($1.0\times10^6$) in 1 mL of a vehicle (fresh DMEM) was intravenously administered from the femoral vein. To the vehicle-administration group (n=7), 1 mL of a vehicle (fresh DMEM) was intravenously administered and motor function and survival period were evaluated. An immunosuppressant cyclosporin A (10 mg/kg) was intraperitoneally administered to all rats every day from the day before MSC and vehicle administration until the day reaching the end-stage.

Results

Figure 8:
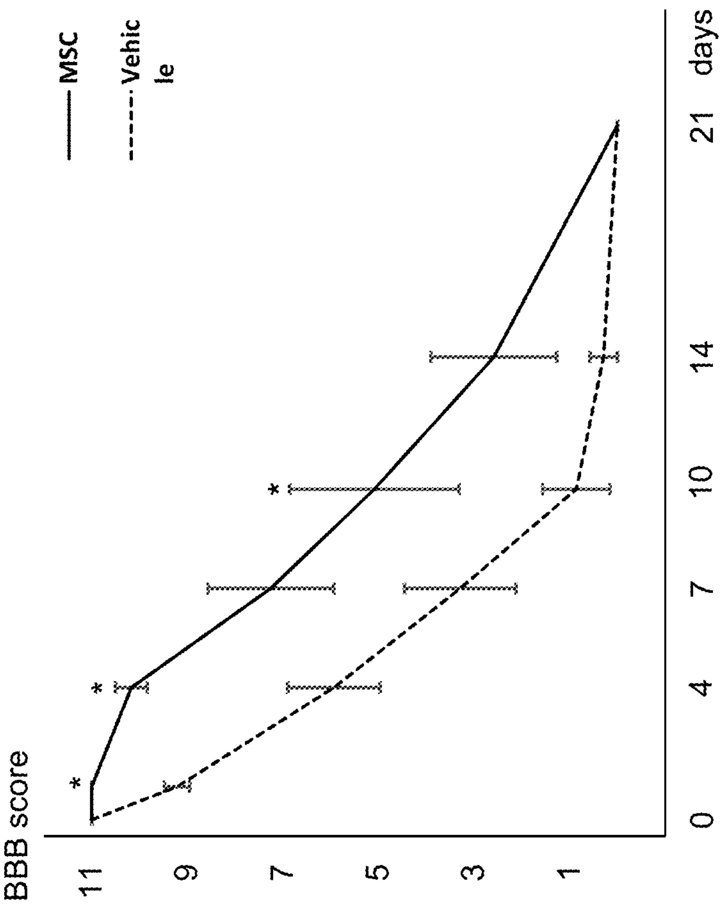
FIG. 8 shows behavioral evaluation of ALS model rats (severe stage) (solid line: MSC administration group, dashed line: vehicle administration group).
Figure 9:
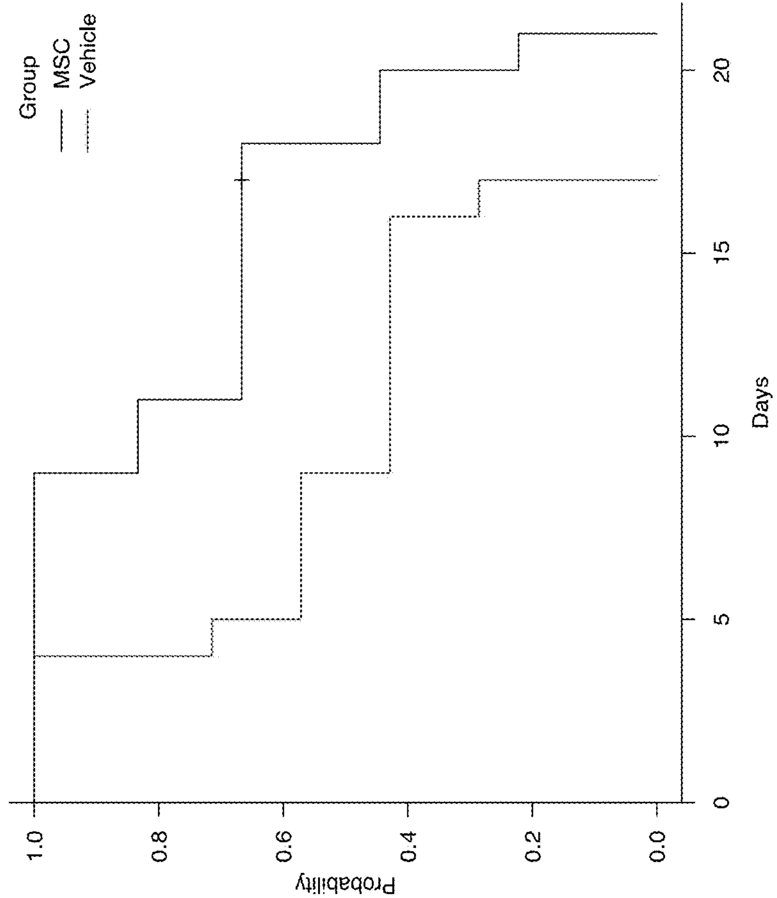
FIG. 9 shows evaluation of survival periods of ALS model rats (severe stage) (upper line: MSC administration group; lower line: vehicle administration group).

The decrease in motor function was significantly suppressed in the MSC-administration group (n=6) as compared with the vehicle-administration group (n=7) (FIG. 8). The survival period was also significantly extended (FIG. 9).

Example 4: Effect of Multiple Doses of MSCs in ALS Model Rat

1. Behavioral Evaluation

Method

MSCs ($1.0\times10^6$) were intravenously administered a plurality of times at a frequency of once every other week to ALS model rats having a BBB score reduced to 15 and exhibiting moderate motor dysfunction. The motor function of the multiple-administration group (n=9) was evaluated based on the BBB score and compared to those of a single administration group (n=5) and vehicle administration group (n=6). An immunosuppressant cyclosporin A (10 mg/kg) was intraperitoneally administered to all rats every day from the day before MSC and vehicle administration to the final evaluation day.

Results

Figure 10:
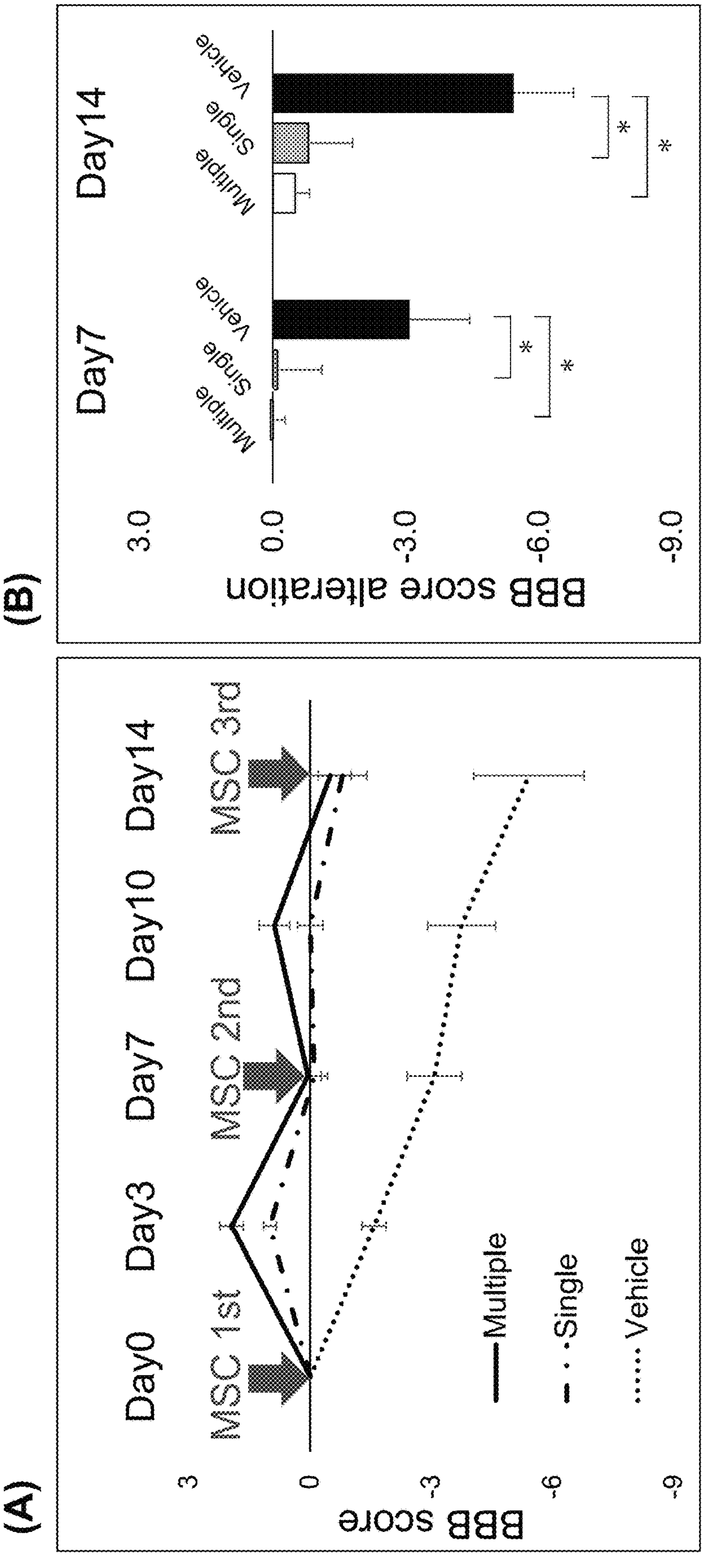
FIG. 10 shows behavioral evaluation of ALS model rats (moderate stage) by multiple MSC administration. (A) BBB score (solid line: MSC multiple administration group; dashed line: MSC single administration group; dotted line: vehicle administration group); (B) BBB score alteration (open white bar: MSC multiple administration group; gray bar: MSC single administration group; solid bar: vehicle administration group).

In the multiple-dose MSC group, improvement in motor function was observed not only in the first administration but also in the second administration (FIG. 10). On both Day 7 and Day 14 from administration, motor function was significantly suppressed as compared with the vehicle-administration group.

2. Long-Term Motor Function

Method

Long-term changes in motor function in the MSC multiple administration group (n=7) were compared with the MSC single administration group (n=6) and the vehicle administration group (n=13). The immunosuppressant cyclosporin A (10 mg/kg) was intraperitoneally administered to all rats every day from the day before MSC and vehicle administration until the day reaching the end-stage.

Results

Figure 11:
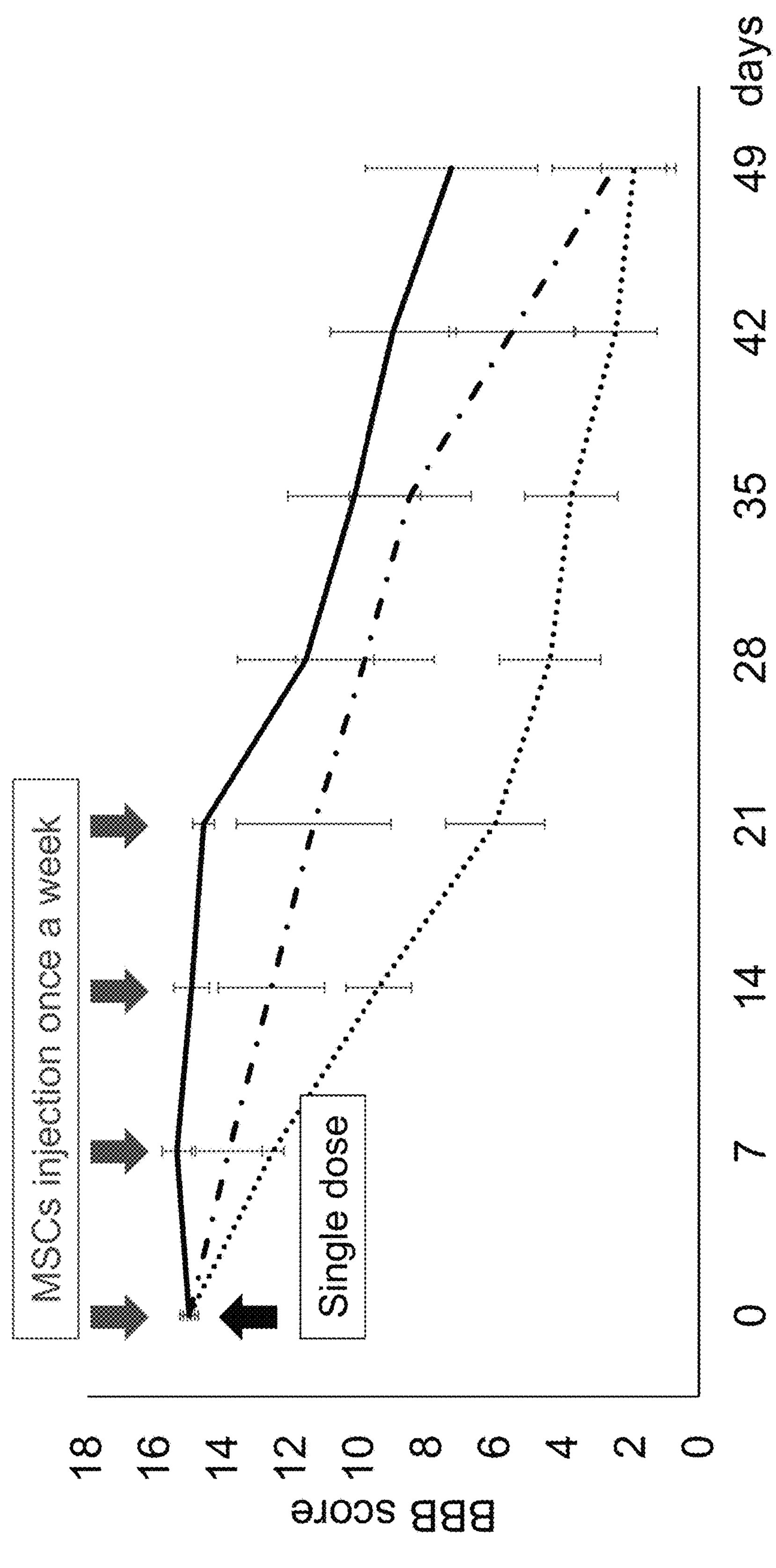
FIG. 11 shows evaluation of long-term motor function of ALS model rats (moderate stage) by multiple MSC administration (solid line: MSC multiple administration group; dashed line: MSC single administration group; dotted line: vehicle administration group).

In the multiple administration group, motor function could be maintained for a longer period of time than in the single administration group and the vehicle administration group (FIG. 11).

3. Survival Period

Method

The survival period of the MSC multiple administration group (n=7) was compared with those of the MSC single administration group (n=6) and the vehicle administration group (n=13).

Results

Figure 12:
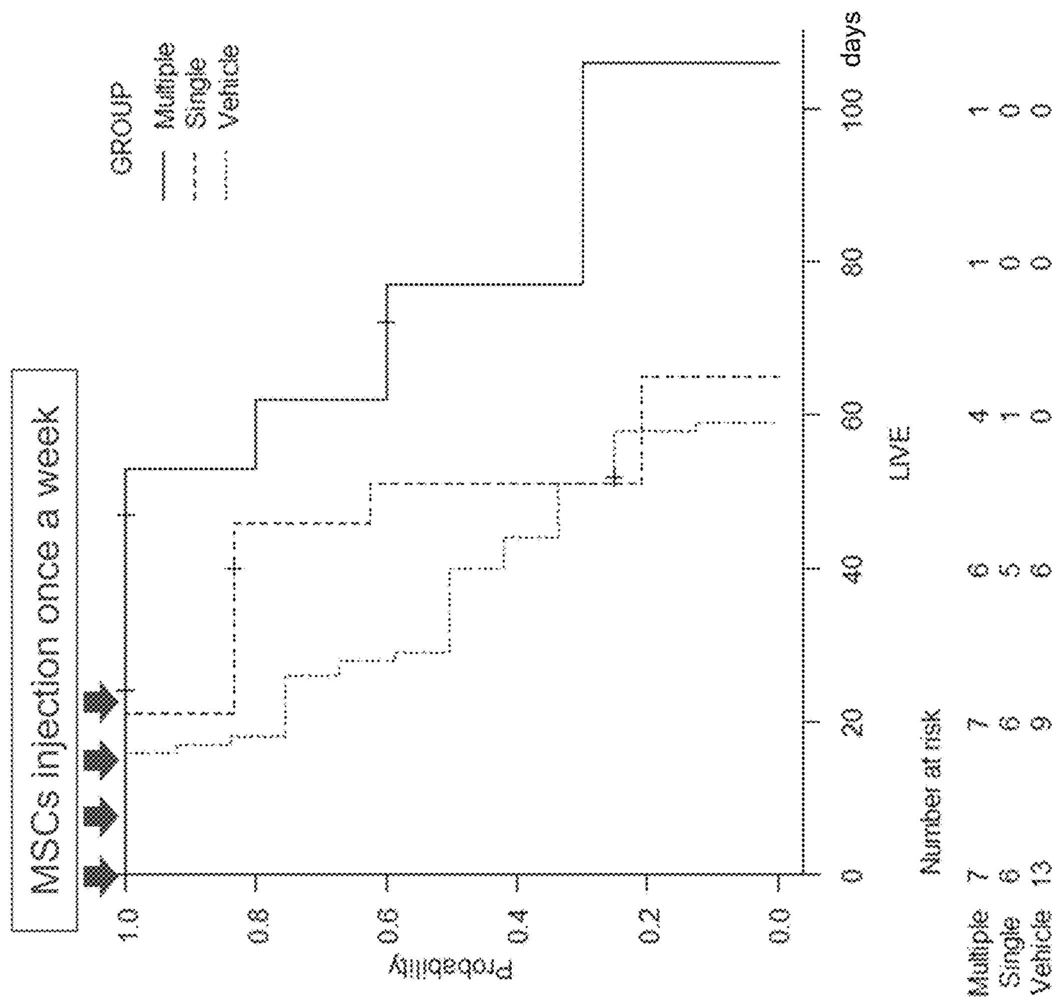
FIG. 12 shows evaluation of survival period of ALS model rats (moderate stage) by multiple MSC administration (solid line: MSC multiple administration group; dashed line: MSC single administration group; dotted line: vehicle administration group).

The survival period was significantly extended in the multiple-administration group compared to the single-administration group and the vehicle-administration group (FIG. 12).

Example 5: Differences in Effect Depending on MSC Dosage in ALS Model Rat

Method

The ALS model rats were divided into three groups based on the MSC dose: low dose group ($1.0\times10^5$, n=3), standard dose ($1.0\times10^6$, n=4), and high dose ($1.0\times10^7$, n=3). MSCs were intravenously administered to the ALS model rats having a BBB score reduced to 15. The BBB score alteration was compared with that of the vehicle-administration group (n=6).

The immunosuppressant cyclosporin A (10 mg/kg) was intraperitoneally administered to all rats every day from the day before MSC and vehicle administration to the final evaluation day.

Results

Figure 13:
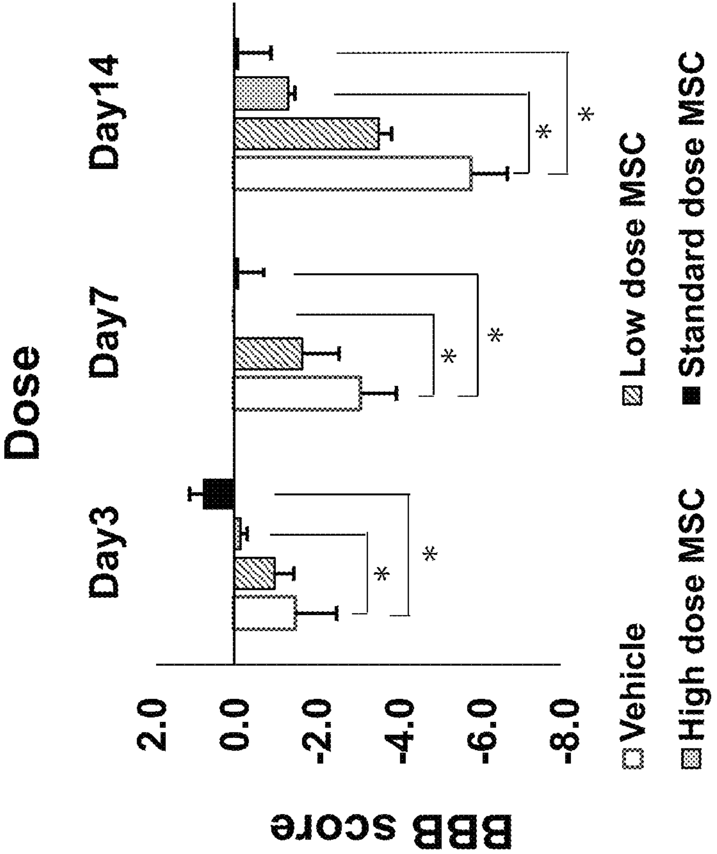
FIG. 13 shows evaluation of MSC dose in ALS model rats (moderate stage) (Day 3, Day 7, Day 14 each in which a vehicle administration group, a low dose MSC administration group ($1.0\times10^5$ cells, n=3), a standard dose MSC administration group ($1.0\times10^6$ cells, n=4), and a high dose MSC administration group ($1.0\times10^7$ cells, n=3) are shown sequentially from the left).

Hypokinesia was significantly suppressed in the standard dose and high dose administration groups (FIG. 13).

Example 6: Differences in Effect Depending on MSC Administration Method in ALS Model Rrat Method Based on MSC administration methods, ALS model rats were divided into two groups: intravenous administration group (n=3) and intraspinal administration group (n=3). Changes in hindlimb motor function were compared with the vehicle intraspinal administration group (n=3). To the intravenous administration group, a solution prepared by dissolving $1.0\times10^6$ MSCs in 1 mL of DMEM was administered from the femoral vein. To the intraspinal administration group, $1.0\times10^5$ MSCs were administered into the cisterna magna using a HAMILTON syringe. An immunosuppressant cyclosporin A (10 mg/kg) was intraperitoneally administered to all rats every day from the day before MSC and vehicle administration to the final evaluation day.

Results

Figure 14:
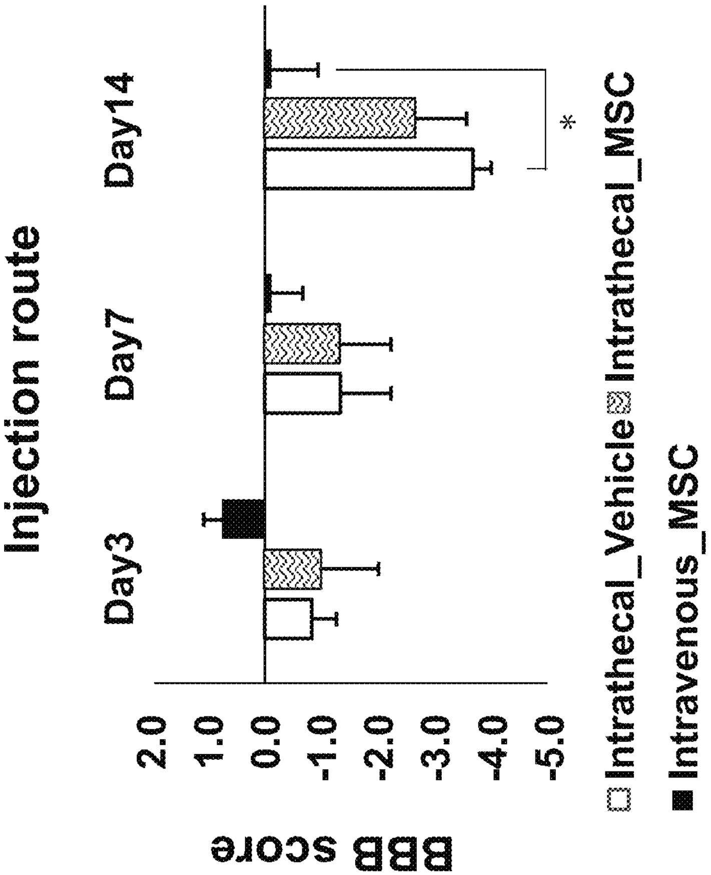
FIG. 14 shows evaluation of MSC administration method in ALS model rats (moderate stage) (Day 3, Day 7, Day 14 each in which a vehicle intraspinal administration group, MSC intraspinal administration group and MSC intravenous administration group are shown sequentially from the left of the graph).

In the evaluation on Day 14 from administration, hypokinesia was significantly suppressed in the intravenous administration group. On Day 3 from administration, improvement of symptoms was confirmed in the intravenous administration group (FIG. 14).

INDUSTRIAL APPLICABILITY

The pharmaceutical composition of the present invention prevents the impairment of BBB/BSCB and simultaneously promoting secretion of neurotrophic factors to suppresses neurological disorders. In this manner, the progression of ALS can be suppressed and the survival period can be extended. According to the present invention, it becomes possible to treat ALS for which an effective therapeutic means has not yet been found.

All publications, patents and patent applications cited herein are incorporated herein by reference in their entirety.

The invention claimed is:

1. A method for treating amyotrophic lateral sclerosis (ALS) comprising intravenously administering two or more doses of a therapeutically effective amount of mesenchymal stem cells derived from bone marrow or blood to a subject in need thereof, wherein the ALS is ALS in a moderate or severe stage corresponding to a stage in a rat ALS model with a Basso, Beattie and Bresnahan (BBB) score of 15 to 8, wherein $1.0\times10^5$ to $1.0\times10^8$ or more mesenchymal stem cells are administered in each dose, wherein the first administration is performed after the subject has developed clinical symptoms of ALS, and wherein the two or more doses are administered at intervals sufficient to maintain a therapeutic effect of a preceding dose.

2. The method according to claim 1, wherein $10^6$ or more mesenchymal stem cells are administered in each dose.

3. The method according to claim 1, wherein the mesenchymal stem cells are mesenchymal stem cells derived from bone marrow or blood of the subject.

4. The method according to claim 1, wherein the mesenchymal stem cells are CD24-negative.

5. The method according to claim 1, wherein the administration of the mesenchymal stem cells suppresses impairment of one or more of the subject's blood-brain-barrier and blood-spinal cord barrier.

6. The method according to claim 1, wherein the administration of the mesenchymal stem cells enhances the expression of neurotrophic factors.

7. The method according to claim 1, wherein $10^7$ or more mesenchymal stem cells are administered in each dose.

8. The method according to claim 1, wherein $10^8$ or more mesenchymal stem cells are administered in each dose.

9. The method according to claim 1, wherein the subject is at a stage of initial paralysis observed in at least one leg.

* * * * *